United States Patent [19]

Fickenscher

[11] Patent Number: 5,231,033
[45] Date of Patent: Jul. 27, 1993

[54] METHOD FOR DETERMINING VON WILLEBRAND FACTOR

[75] Inventor: Karl Fickenscher, Marburg, Fed. Rep. of Germany

[73] Assignee: Behringwerke Aktiengesellschaft, Marburg, Fed. Rep. of Germany

[21] Appl. No.: 704,948

[22] Filed: May 23, 1991

[30] Foreign Application Priority Data

May 25, 1990 [DE] Fed. Rep. of Germany ........ 4016885

[51] Int. Cl.⁵ .......................................... G01N 21/82
[52] U.S. Cl. ...................................... 436/70; 436/45; 436/69; 356/39; 435/13
[58] Field of Search .............. 436/69, 70, 45; 356/39; 424/3, 542; 435/2, 4, 13, 29; 422/73

[56] References Cited

U.S. PATENT DOCUMENTS

| 4,640,896 | 2/1987 | Farrell et al. | 436/34 |
| 4,777,141 | 10/1988 | Calzi et al. | 436/69 |
| 4,936,674 | 6/1990 | Ikeda et al. | 356/39 |

FOREIGN PATENT DOCUMENTS 0049265  3/1985  Japan .

OTHER PUBLICATIONS

Ruggeri et al., "von Willebrand Factor and von Willebrand Disease", Blood, vol. 70, No. 4, (Oct.), 1987, pp. 895-904.

Macfarlane et al., "A Method for Assaying von Willebrand Factor (Ristocetin Cofactor)", Thrombos, Diathes, heamorrh, (Stuttg.) 1975, 34, 306.

Bowie, D. M., "von Willebrand's Disease, Clinical Picture, Diagnosis, and Treatment", Clinics in Laboratory Medicine, vol. 4, No. 2, Jun. 1984, pp. 303-317.

Goodall et al., "An Immunoradiometric Assay For Human Factor VIII/von Willebrand Factor (VII:vWF) Using a Monoclonal Antibody That Defines A Function Epitope", British Journal of Haematology, 1985, 59, 565-577.

Y. Sufan et al., "An Immunoradiometric Assay for Factor VII Related Antigen (VIIRAg) Using Two Monoclonal Antibodies—Comparison with Polyclonal Rabbit Antibodies for Use in von Willebrand's Disease Diagnosis", Thromb. Haemost., vol. 52, (1984), pp. 250-252.

*Primary Examiner*—James C. Housel
*Assistant Examiner*—David Redding
*Attorney, Agent, or Firm*—Finnegan, Henderson, Farabow, Garrett & Dunner

[57] ABSTRACT

The invention relates to a method for the functional determination of von Willebrand factor by determination of the sedimentation rate of platelets in the presence of ristocetin during centrifugation.

6 Claims, No Drawings

METHOD FOR DETERMINING VON WILLEBRAND FACTOR

The invention relates to a method for the functional determination of von Willebrand factor by determination of the sedimentation rate of platelets in the presence of ristocetin, which can also be applied to centrifugal analyzers.

The von Willebrand factor (factor VIII:vWF) is the high molecular weight portion of the factor VIII molecule and, owing to its interaction with platelets and factor VIIIc, plays an important part in the coagulation process. Functional deficits or quantitative deficiencies result in a tendency to bleeding.

The von Willebrand syndrome is an acquired or hereditary disease which is attributable to a quantitative or qualitative deficiency of F VIII:vWF (Ruggeri, Z. M. & Zimmerman, T. S. 1987, Blood 70: 895-904). The hereditary type is probably the commonest inherited coagulation disorder (Bowie, E. J. W., 1984, Clin. Lab. Med. 4, 303-317). Several types and subtypes of the disorder are known. It is characteristic of type I that a reduced amount of F VIII:vWF is present. The characteristic of type II is qualitative deficiencies, while the amount is normal. Type II disorders are further divided into various subtypes depending on whether changes in the multimer structure are affected or whether they are functional abnormalities.

Determination of von Willebrand factor can be carried out with various assay methods depending on which property is to be tested. Available for determination of the antigen are ELISA, Laurell immunoelectrophoresis and other immunological assays (Goodall, A. H. et al. 1985, Brit. J. Haematol. 59: 565-577; Sultan, Y. et al. 1984, Thromb. Haemost. 52: 250-252).

Methods for the functional determination of factor VIII:vWF using native platelets which are stabilized or also contained in the sample are known. The sample is added to a stirred suspension of native or fixed platelets in the presence of ristocetin, and the rate of change in the transmission due to the aggregation which is induced is determined (Macfarlane, D. E. et al., 1975, Thromb. Diathes. Haemorrh. 34: 306).

Platelets have, both in the native state and in fixed form, as are employed for determination of von Willebrand factor, the disadvantageous property of rapid sedimentation because of their relatively high specific gravity. This is why the assay systems customary to date operate either in stirred cuvettes in aggregometers or with very low thickness layers on assay plates. To date it has been possible to determine von Willebrand factor only manually, and thus also only with the inaccuracies related thereto.

Hence the object of the invention was to find a method which makes completely automatic, precise determination of von Willebrand factor possible.

The invention thus relates to a method for the determination of von Willebrand factor, where a sample of a biological material, for example plasma, is incubated with a reagent which contains, for example, platelets and ristocetin, and the extent of aggregation is determined by the change in the turbidity, in that the aggregates which are formed undergo controlled sedimentation owing to a suitable radial acceleration during a centrifugation.

An example of a possible measure of the sedimentation rate is to determine the time which elapses until the turbidity existing in the assay mixture has changed to a preset value. Another possibility comprises continuous determination and evaluation of the change in the turbidity.

Also made possible thereby is determination of the functional capacity of blood platelets when platelet-rich plasma is employed.

In a preferred embodiment of the invention, the sample (200 $\mu$l of platelet-poor plasma) is placed in one chamber, and a reagent (composed of 50-200 $\mu$l of stabilized platelets and ristocetin) is placed in a second chamber of a centrifugal analyzer rotor. Sample and reagent are mixed by centrifugation, and then the reaction is followed optically at 10-1000 x g, preferably at 20 to 200 x g. The measurement can be carried out at every wavelength which permits determination of a turbidity. A measurement wavelength of 405 nm may mentioned here by way of example; a wavelength which is usually already present on appropriate centrifugal analyzers. Centrifugal analyzers are known per se to the person skilled in the art.

The determination can be carried out at 10°-40° C., preferably at 20°-40° C., very particularly preferably at 37° C.

In a preferred embodiment, the time which elapses from the start of the reaction until the optical density has changed by, for example, 0.03 A is determined as a measure of the sedimentation rate. The time which is found is inversely proportional to the content of factor VIII:vWF.

The embodiment indicated in the example is very particularly preferred.

In another embodiment, the measurement of the sedimentation rate can also be carried out with the aid of other nephelometric and turbidimetric methods known per se to the person skilled in the art.

It has been found that the described method can be used to determine the activity of the von Willebrand factor present in platelet-poor plasma both sensitively and precisely, as well as straightforwardly. The assay is insensitive to F VIII:C (up to 400%). It is possible to employ commercially available reagents (for example von Willebrand factor from Behringwerke AG, D-3550 Marburg).

Compared with known methods, the method according to the invention is distinguished by its simplicity, sensitivity and ease of automation.

EXAMPLE

Determination of von Willebrand Factor in a Plasma Sample

For the calibration, 100%, 75%, 50%, 25%, 10% and 0% dilutions are prepared of a platelet-poor normal plasma pool in phosphate-buffered isotonic sodium chloride solution. The standards and the samples are measured as described hereinafter.

15 $\mu$l of sample (platelet-poor plasma) and 200 $\mu$l of reagent (formalin-fixed platelets and ristocetin) are introduced and mixed by centrifugation. The reaction is carried out at 100 x g in a centrifugal analyzer (ACL 300 from IL). The measurement was carried out at 405 nm. However, every other wavelength at which the turbidity of the liquid owing to the particulate blood platelets can be determined would be suitable likewise. Then the time for the optical density in the mixture to fall by 0.03 A was determined. The time which is found is inversely proportional to the content of von Willebrand factor.

I claim:

1. A method for the determination of von Willebrand factor comprising the steps of:
   a) incubating a sample of a biological material with a reagent which contains platelets and ristocetin,
   b) determining photometrically the change in the turbidity, wherein aggregates which are formed undergo controlled sedimentation owing to a suitable radial acceleration during a centrifugation, thereby providing a measured sedimentation rate, and
   c) comparing the measured sedimentation rate with a calibration curve to determine the amount of von Willebrand factor.

2. The method as claimed in claim 1, wherein platelet-poor plasma is employed as the sample for the determination of von Willebrand factor.

3. The method as claimed in claim 2, wherein stabilized platelets are employed as the reagent for the determination of von Willebrand factor 4. The method as claimed in claim 2, wherein ristocetin is used as aggregation inducer.

5. The method as claimed in claim 1, wherein the radial acceleration is between 10 and 1000 x g.

6. The method as claimed in claim 1, wherein the biological material is plasma.

* * * * *